(12) United States Patent
Venon et al.

(10) Patent No.: US 8,886,726 B2
(45) Date of Patent: Nov. 11, 2014

(54) SYSTEMS AND METHODS FOR INTERACTIVE SMART MEDICAL COMMUNICATION AND COLLABORATION

(75) Inventors: Medhi Venon, Whitefish Bay, WI (US); Elad Shoushan, Herzliya (IL); Orit Moshkovitz, Givat Shmuel (IL)

(73) Assignee: General Electric Company, Schenectady, NY (US)

(*) Notice: Subject to any disclaimer, the term of this patent is extended or adjusted under 35 U.S.C. 154(b) by 590 days.

(21) Appl. No.: 12/979,524

(22) Filed: Dec. 28, 2010

(65) Prior Publication Data

US 2012/0166546 A1 Jun. 28, 2012

(51) Int. Cl.
*G06F 13/00* (2006.01)
*G06F 19/00* (2011.01)

(52) U.S. Cl.
CPC .......... *G06F 19/3425* (2013.01); *G06F 19/321* (2013.01)
USPC ....................................................... 709/205

(58) Field of Classification Search
CPC ........................... G06F 19/3425; G06F 19/321

USPC .......................................................... 709/205
See application file for complete search history.

(56) References Cited

U.S. PATENT DOCUMENTS

2011/0126127 A1* 5/2011 Mariotti et al. ............... 715/753

* cited by examiner

*Primary Examiner* — Robert B Harrell
(74) *Attorney, Agent, or Firm* — Hanley, Flight and Zimmerman, LLC

(57) ABSTRACT

Certain examples provide collaboration systems, apparatus, and methods to facilitate automated command recognition and execution in collaborative communication. An example system includes a communication interface to accept a communication input in an electronic collaboration session regarding clinical content. The system also includes a collaboration engine to automatically analyze the input to identify one or more instructions corresponding to the input and to automatically execute the identified one or more instructions with respect to content associated with the collaboration session. The collaboration engine is to provide results of the execution of the identified one or more instructions to at least one collaborator in the collaboration session.

23 Claims, 14 Drawing Sheets ized reading and review of diagnostic images. More particularly, the present invention relates to collaboration and real-time (including substantially real-time) sharing of information related to diagnostic images.

SYSTEMS AND METHODS FOR INTERACTIVE SMART MEDICAL COMMUNICATION AND COLLABORATION

FIELD

The present generally relates to computerizing reading and review of diagnostic images. More particularly, the present invention relates to collaboration and real-time (including substantially real-time) sharing of information related to diagnostic images.

BACKGROUND

In many cases, in order to diagnose a disease or injury, a medical scanning device (e.g., a computed tomography (CT) scanner, magnetic resonance imager (MRI), ultrasound machine, etc.) is used to capture an image of some portion of a patient's anatomy. After the acquisition of the image, a trained physician (e.g., radiologist) reviews the created images (usually on a computer monitor), renders an interpretation of findings and prescribes an appropriate action. This example becomes more complex in that current diagnostic imaging departments provide extensive information regarding the human anatomy and functional performance presented through large numbers of two- and three-dimensional images requiring interpretation. Diligent interpretation of these images requires following of a strict workflow, and each step of the workflow presumes visual presentation in certain order of certain image series from one or multiple exams and application of certain tools for manipulation of the images (including but not limited to image scrolling, brightness/contrast, linear and area measurements, etc.).

BRIEF SUMMARY

Certain embodiments of the present invention provide systems, apparatus, and methods for communication, collaboration, and automatic command execution in conjunction with collaboration.

Certain examples provide a computer-implemented method for automated command recognition and execution in collaborative communication. The method includes accepting a communication input in an electronic collaboration session regarding clinical content. The method also includes automatically analyzing the input to identify one or more instructions corresponding to the input. The method includes automatically executing the identified one or more instructions with respect to content associated with the collaboration session. The method includes providing results of the execution of the identified one or more instructions to at least one collaborator in the collaboration session.

Certain examples provide a tangible computer-readable storage medium having a set of instructions stored thereon which, when executed, instruct a processor to implement a method for automated command recognition and execution in collaborative communication. The method includes accepting a communication input in an electronic collaboration session regarding clinical content. The method also includes automatically analyzing the input to identify one or more instructions corresponding to the input. The method includes automatically executing the identified one or more instructions with respect to content associated with the collaboration session. The method includes providing results of the execution of the identified one or more instructions to at least one collaborator in the collaboration session.

Certain examples provide a collaboration system to facilitate automated command recognition and execution in collaborative communication. The system includes a communication interface to accept a communication input in an electronic collaboration session regarding clinical content. The system also includes a collaboration engine to automatically analyze the input to identify one or more instructions corresponding to the input and to automatically execute the identified one or more instructions with respect to content associated with the collaboration session. The collaboration engine is to provide results of the execution of the identified one or more instructions to at least one collaborator in the collaboration session.

Figure 1:
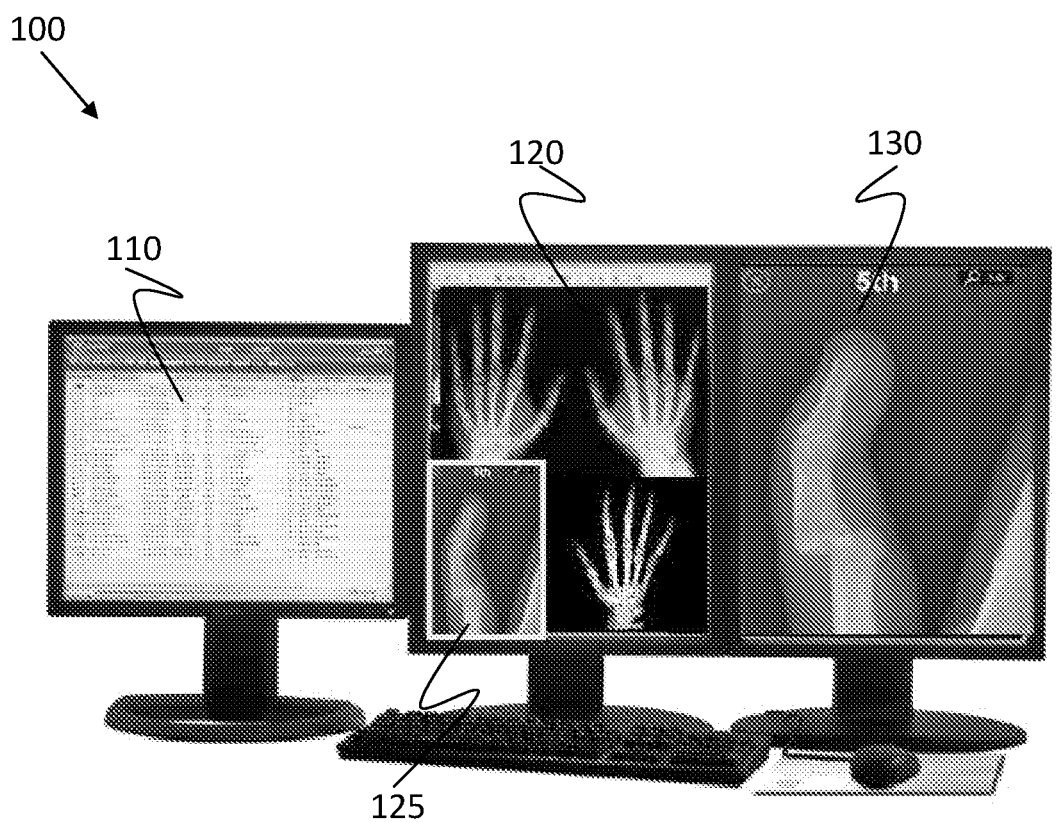
FIG. 1 illustrates an example multi-monitor configuration used by a radiologist to perform an image analysis or reading.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, Blu-ray, etc. storing the software and/or firmware.

Certain examples help facilitate computerized reading of diagnostic images. Certain examples relate to any clinical information system used for collaboration and sharing of real-time (including substantially real-time accounting for system, transmission, and/or memory access delay, for example) information related to visualization and/or multimedia objects. Visualization objects can include but are not limited to images, reports, and results (e.g., lab, quantitative, and/or qualitative analysis post- and/or pre-reading), for example. Multimedia objects can include but are not limited to audio and/or video comments from one or more of the collaborators, images, documents, audio and/or video of references materials, for example Certain examples help to address challenges related to instant and ad hoc collaboration use cases between medical professionals around a region of interest or a patient case, which might involve consultation between two or many radiologists to confirm findings and/or focus diagnostics during a radiologist's reading workflow and/or to define a way to proceed in patient diagnosis and/or treatment. For example, with a stroke case, collaborative work can be facilitated between multi-disciplinary medical teams to provide a fast and accurate response. Certain examples help improve a resident workflow by providing quick consultation with radiologists on certain cases. Certain examples help improve the workflow of a multi-disciplinary medical team to address emergency and/or critical care situations. Certain examples allow each collaborating user to leverage tool set(s) (e.g., advanced processing, measurements, predefined setup, etc.) available on his or her respective device and perform parallel reading without affecting each other's views. This evidence sharing allows users to collaborate while maximizing each user's ability to manipulate evidence concurrently.

Certain examples help simplify an end user experience during a collaboration session between two doctors. While current collaboration tools offer basic approaches to provide hyperlink and other mechanism to link content of messages, certain example systems, apparatus, and methods described herein provide an engine to process content of collaboration messages and convert a portion of a message to one or more actions associated with current evidence under review. For example, if a sender mentions, in a message, a specific measurement to be obtained or a specific automated analysis to conduct, the message is processed by the engine to automatically request an application to perform those action(s) and present the results of the request to the user. The user can then make fine adjustments to the results, for example.

Certain examples help facilitate diagnostic reading of digital medical exams, such as digital radiology imaging. In many cases, in order to diagnose a disease or injury, a medical scanning device (e.g., a computed tomography (CT) scanner, magnetic resonance imager (MRI), ultrasound machine, etc.) is used to capture an image of some portion of a patient's anatomy. After the acquisition of the image, a trained physician (e.g., radiologist) reviews the created images (usually on a computer monitor), renders an interpretation of findings and prescribes an appropriate action. This example becomes more complex in that current diagnostic imaging departments provide extensive information regarding the human anatomy and functional performance presented through large numbers of two- and three-dimensional images requiring interpretation. Diligent interpretation of these images requires following of a strict workflow, and each step of the workflow presumes visual presentation in certain order of certain image series from one or multiple exams and application of certain tools for manipulation of the images (including but not limited to image scrolling, brightness/contrast, linear and area measurements, etc.).

Often a second opinion from a specialist or peer in the same field is required and/or desired, and the person might not be physically present at the same workstation to view the same images. In order to compensate for this, the reading radiologist may invoke a sharing session to reach out to the targeted colleague for discussion of the case. The radiologist performing this collaboration may want to preserve his or her own reading space to manipulate and view an image, while utilizing a different view to debate findings with others as well as offer a set of automation tools. Certain examples provide advanced integration of a collaboration environment with one or more tools and applications enabling seamless and easy collaborative transactions between the primary radiologist in charge of the exam reading and the consulting physician(s).

An example collaboration engine helps trigger actions in one or more applications based on message content, for example. For example, if a sender types "go to image #65 and apply zoom 2.0 on the lower corner", a collaboration component performs such a request (e.g., prefetch and presentation setting) and allow the user to access the result at his or her convenience. Thus, certain examples enhance the collaboration experience to allow users to focus on exchanging feedback while the application streamlines the users' input in the form of texting, messaging, and/or graphical insertion between sender and receiver.

Certain examples provide a "power word" mode that is multi-directional such that any user (e.g., a primary radiologist who is in charge on an exam, a consulting physician that either has mobile device or has access to the exam from a remote workstation, etc.) can initiate the "power word" process by typing, dictating, etc., a message that is translated by a collaboration engine and sent as a set of actions to other workstation(s) and/or mobile device(s) that display results.

Automation of text processing in a message helps reduce or avoid performance of manual actions by a user, can be extended to sharing data by automatically sending the data using an email or short message service (SMS), for example. If a person asks: "Can you email me or can you text me?", for example, a collaboration exchange can automatically be prepared. Using automated text processing, a user can avoid performing precise measurements and/or other actions with respect to images that could be tedious if the user is viewing and manipulating the image on a mobile device, for example. An example "power word" mode helps enable the user to focus on the collaboration while each device is able to fulfill or prepare the request automatically based on user message input.

FIG. 1 illustrates an example multi-monitor configuration 100 used by a radiologist to perform an image analysis or reading. Using the image reading system 100, a radiologist selects a study 120 that he or she would like to review from a worklist 110. The radiologist performs an analysis and, for example, adds one or more measurements to one or more images in the study 120. For example, the radiologist selects 125 an image 130 from the study 120 for larger display and review.

Figure 2:
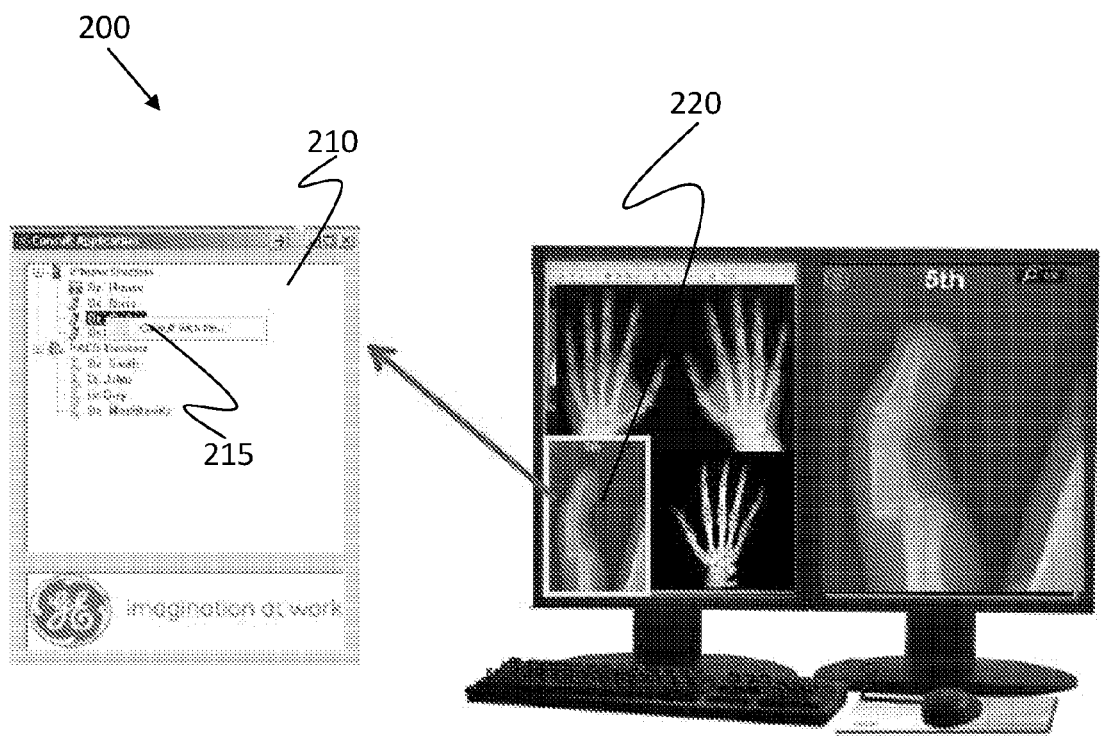
FIG. 2 depicts an example consultation selection with an available specialist.

As shown in the example of FIG. 2, a radiologist opens a consultation application 210 and selects a specialist 215 from a list of available mobile device users for a consultation regarding the selected study image(s) 220. The system 200 allows a user to categorize and select one or more users for collaboration, for example.

Figure 3:
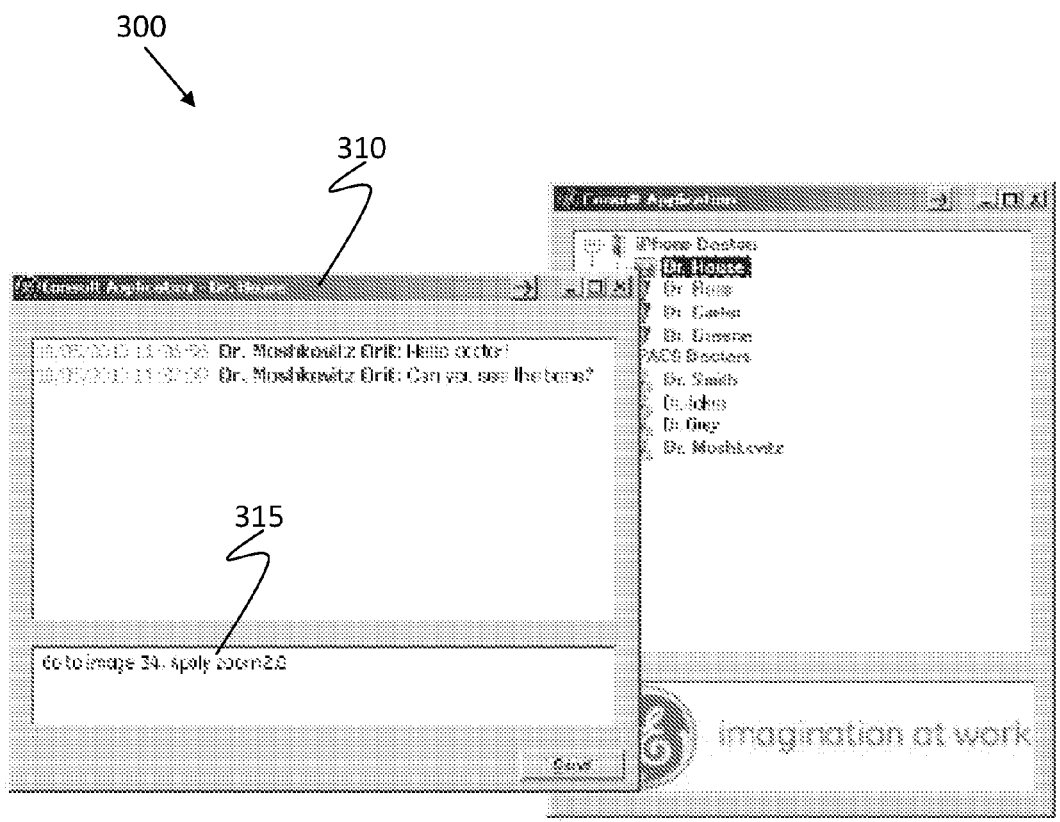
FIG. 3 illustrates an example system for collaboration and user instruction.

As illustrated in the example of FIG. 3, a user can provide one or more instructions 315 via a collaboration session 310. For example, a radiologist can type a specific measurement and/or a specific automated analysis to be performed on the selected study (e.g., one or more images in the study). As shown in an example system 300, the radiologist enters "Go to image 34. Apply zoom 2.0."

Figure 4:
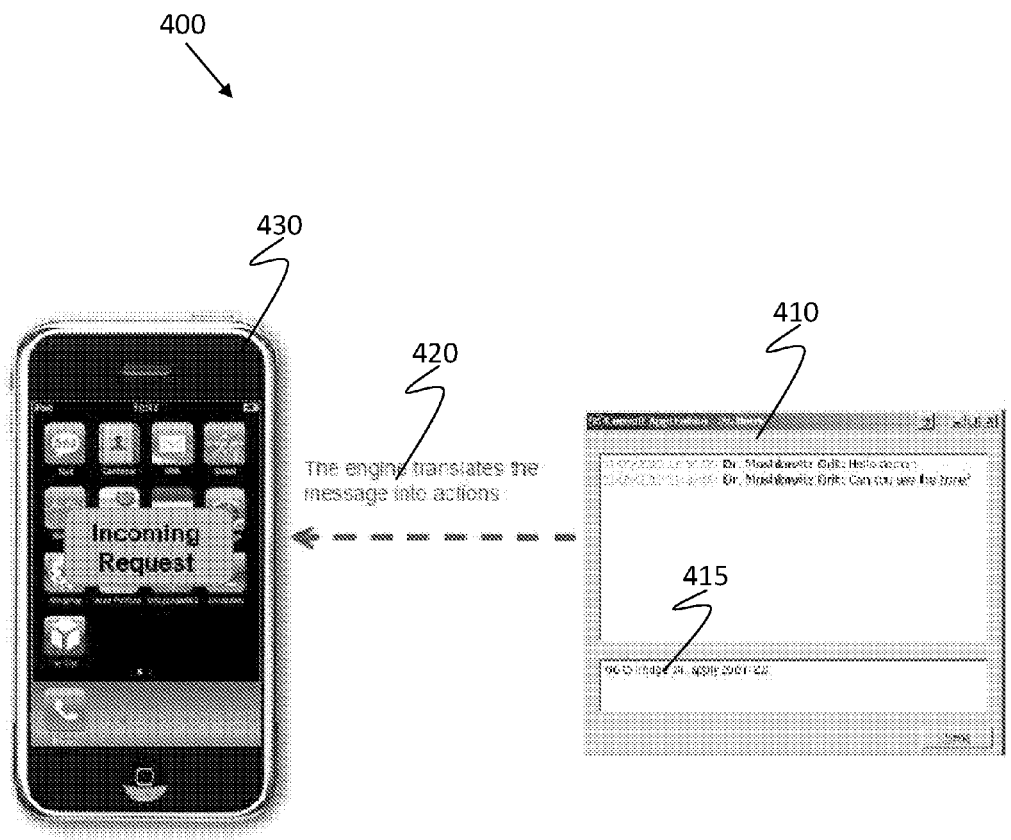
FIG. 4 shows an example message translation from a collaboration session into action by a collaborating device.

As shown in the example of FIG. 4, a collaboration engine 420 translates a user message 415 from a collaboration messaging window 410. The engine 420 translates the message 415 into one or more actions to be performed. The action(s) can be performed in an example system 400 by the other collaborating user's mobile device 430 (e.g., Apple iPhone™, Apple iPad™, BlackBerry™ smartphone, and/or other smart phone, tablet, laptop, etc.), for example. Behind the scenes, the collaboration engine 420 processes content of the message 415 and converts the message into one or more actions for the current evidence under review, for example.

Figure 5:
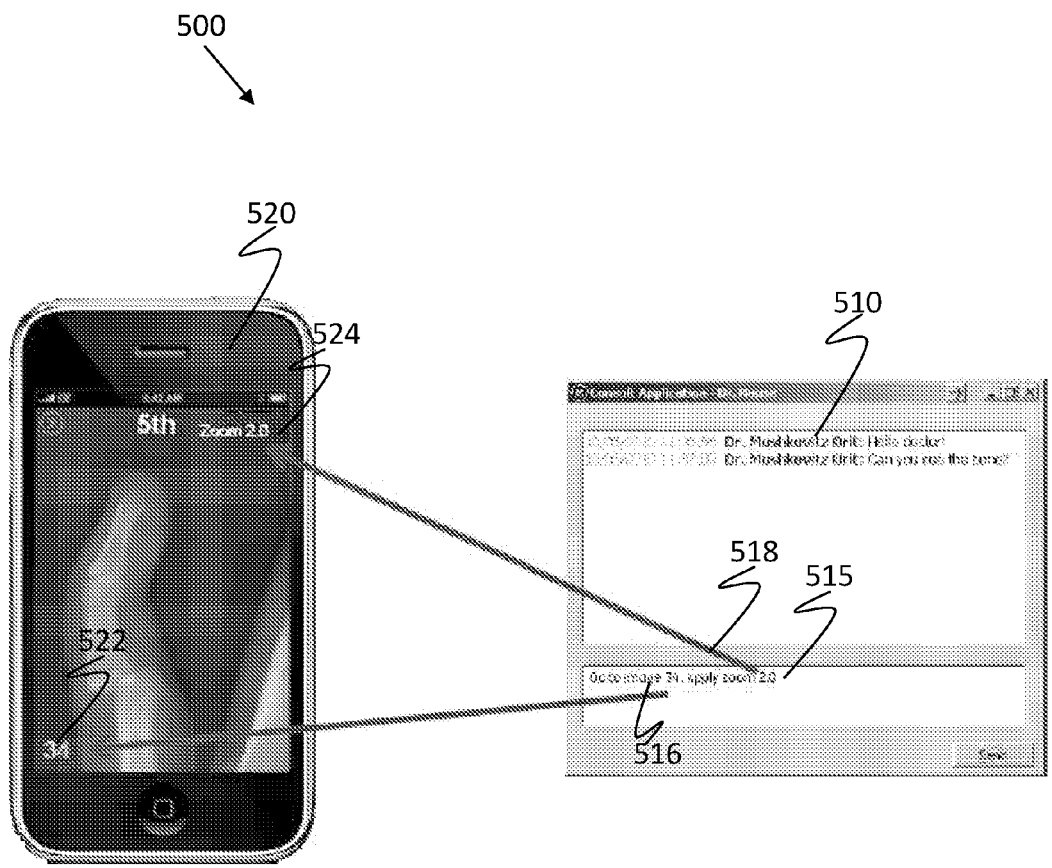
FIG. 5 illustrates an example collaboration system in which an action requested in a message by one user results in a change at a device of another user involved in the collaboration.

FIG. 5 illustrates an example collaboration system 500 in which an action requested in a message by one user results in a change at a device of another user involved in the collaboration. For example, a message 515 provided by a user in a collaboration session 510 includes a first instruction 516 and a second instruction 518. In the example shown in FIG. 5, the first instruction 516 requests movement and/or retrieval of image number thirty-four (34). The second instruction 518 in the example 500 requests a zoom at a factor of two (2.0). As demonstrated in the example of FIG. 5, at a collaborating user's mobile device 520, image 34 is displayed 522, at a zoom factor 524 of 2.0. A mobile device 520 application performs the set of actions 516, 518 generated by a collaboration engine and presents results 522, 524 of the refinement for review and adjustment by the user, for example.

Figure 6:
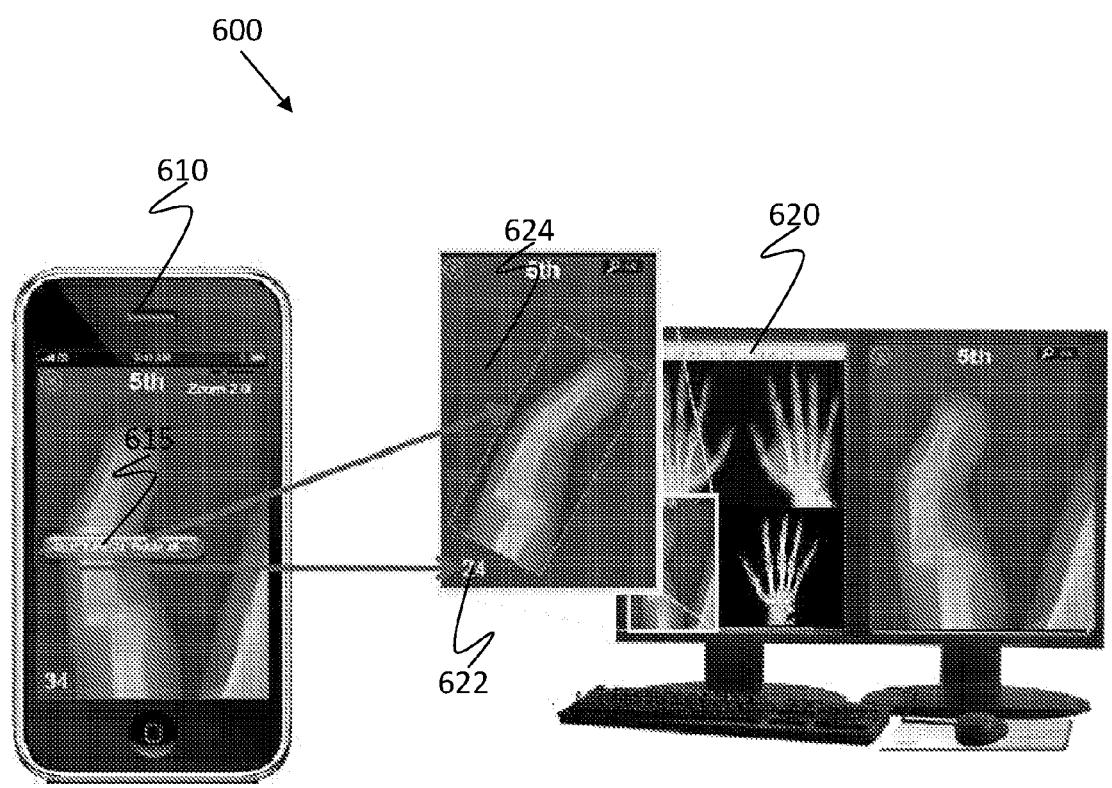
FIG. 6 illustrates an example collaboration system in which a mobile device user initiates the collaboration process.

FIG. 6 illustrates an example collaboration system 600 in which a mobile device user initiates the collaboration process. For example, a collaboration process can be initiated and/or conducted bi-directionally, with a mobile and/or desktop user initiating and/or continuing a collaboration exchange and message-based commands. For example, a mobile device 610 user can initiate a power words process by typing a message 615 in a collaboration session to be translated by a collaboration engine. The translated message is sent as a series of actions to a workstation 620 participating in the collaboration. Results are presented to a collaborating user on the workstation display(s) 620.

For example, a mobile device 610 user may specify "Go to frame 24. Rotate 45." in the message 615. The collaboration engine translates the message into a series of commands/instructions that instruct the workstation 620 to display an image 622 at frame 24, rotated 45 degrees 624. With a gesture on a touch screen, for example, the system 600 can translate an action into a message for other connected, collaborating user(s).

Figure 7:
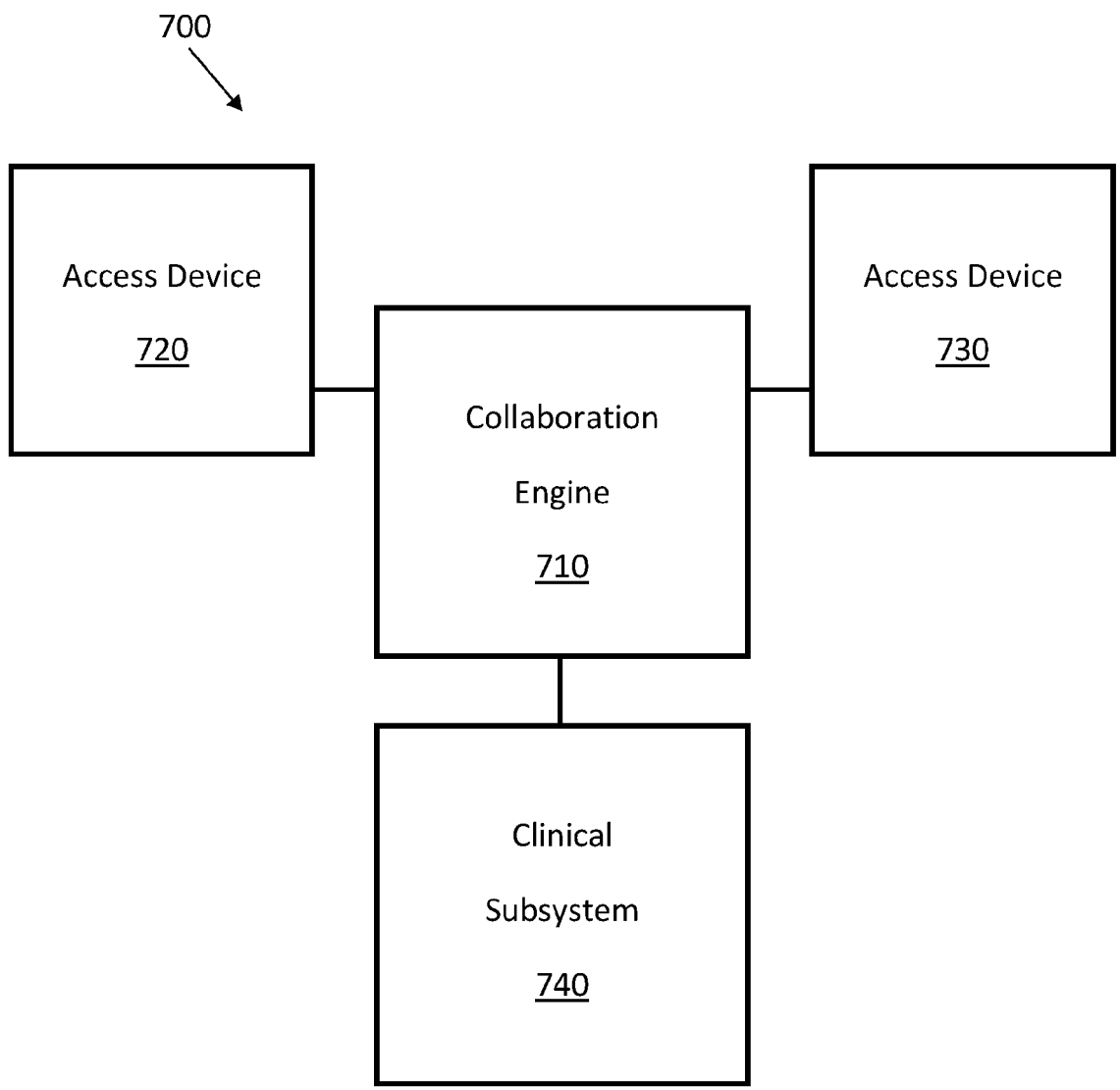
FIG. 7 illustrates an example collaboration system to provide communication exchange and communication content processing to automatically facilitate execution of command(s) related to the content of the exchanged communication.

FIG. 7 illustrates an example collaboration system 700 providing communication exchange and communication content processing to automatically facilitate execution of command(s) related to the content of the exchanged communication. The example system 700 includes a collaboration engine 710, a first access device 720, a second access device 730, and a clinical subsystem 740. The components of the system 700 can be implemented alone and/or in combination using one or more of hardware, software, and firmware, for example. Each of the components of the system 700 includes a processor and memory to send and/or receive data, process instructions and associated data, etc. The first and second access devices 720, 730 can be implemented as handheld/mobile devices (e.g., tablet, smart phone, personal digital assistant, etc.) and/or as laptop/desktop computer devices, for example. The clinical subsystem 740 can include one or more of a data source, a healthcare information systems (a radiology information system (RIS), picture archiving and communication system (PACS), cardiovascular information system (CVIS), hospital information system (HIS), laboratory information (LIS), electronic medical record (EMR), electronic health record (EHR), personal health record (PHR), etc.), an image/data archive, an imaging modality (e.g., x-ray, ultrasound, magnetic resonance imager, etc.). The collaboration engine 710 can be implemented separately and/or as a component of one or more of the first access device 720, second access device 730, and/or clinical subsystem 740, for example.

Using the collaboration engine 710, the first access device 720 can initiate a communication and/or other collaboration session with the second access device 730. In addition to conveying information in a session between the first and second access devices 720, 730, content of the communication (e.g., words, images/icons, audio and/or video clips, etc.) can be recognized by the collaboration engine 710 to trigger an action at one or more of the first access device 720, second access device 730, and clinical subsystem 740, for example.

For example, the collaboration engine 710 can link the content of messages between the first and second access devices 720, 730 to link an application interface and/or events to automate execution of an application component based on the message content. In an example, content of a message linked to application events from the message content can be highlighted. In an example, action(s) can be prefetched and/or otherwise triggered by the collaboration engine 710 based on queue message(s) before one or more end users access the collaboration session. In an example, message content can be highlighted and linked to application events from the message content and third party application(s) integrated with a host application. For example, if an external application interfaces with the collaboration application, a content processing engine can enable automation of the execution of functions of the third party application when using the collaboration capability.

Certain examples help enable prefetch for preparation and presentation of a collaboration session based on an initial inquiry of a sender. Certain examples help enable the collaboration session to propose a set of recommended actions from initial collaboration inquiries linked to a type of procedure and/or an order set.

In an example, a collaboration application is able to process an audio message to link an application interface and/or events to automate execution of an application component based on the message content. In an example, a user action can be translated to a short message service (SMS) message, which can be edited before sending. In an example, a power word capability is extended to a third party application such as email, phone, SMS, calendar, and/or other application.

Figure 8:
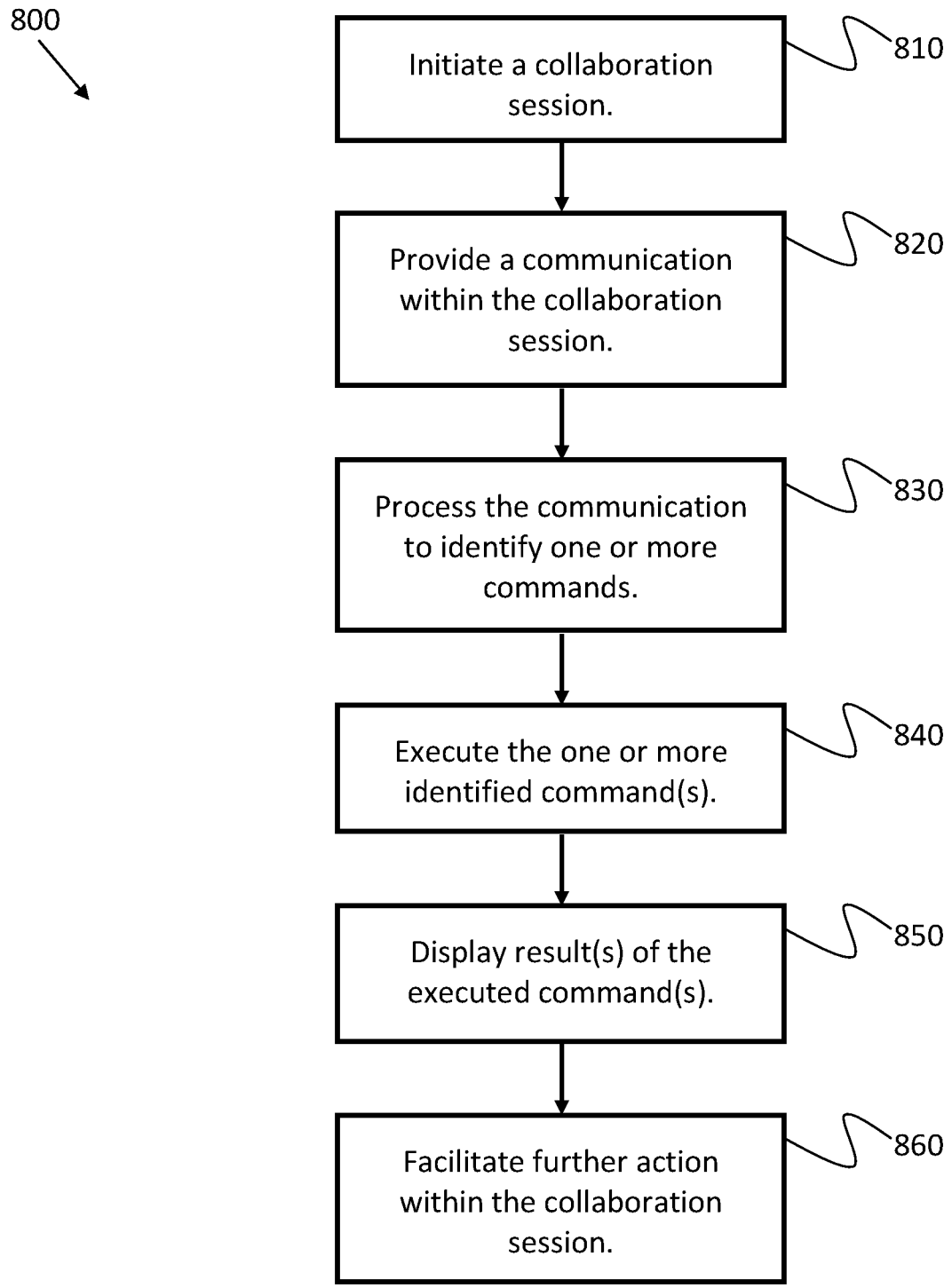
FIG. 8 depicts a flow diagram for an example method for collaborative communication including automated command recognition and execution.
Figure 9:
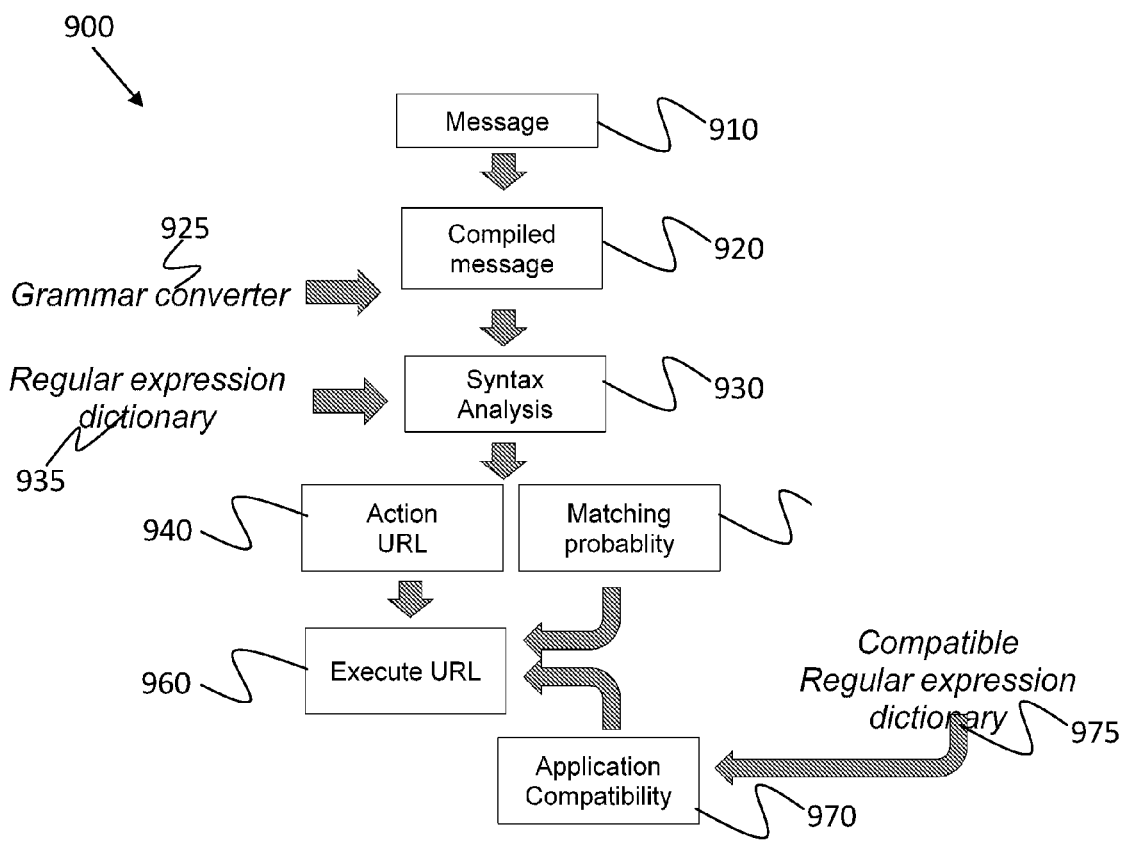
FIG. 9 depicts a flow diagram for an example method for processing communication input to identify one or more commands for execution.

FIGS. 8-9 depict an example flow diagram representative of processes that can be implemented using, for example, computer readable instructions that can be used to facilitate reviewing of anatomical images and related clinical evidence.

The example processes of FIGS. 8-9 can be performed using a processor, a controller and/or any other suitable processing device. For example, the example processes of FIGS. 8-9 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 8-9 can be implemented using coded instructions (e.g., computer readable instructions) stored on a non-transitory computer readable medium such as a flash memory, a read-only memory (ROM), a random-access memory (RAM), a CD, a DVD, a Blu-ray, a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 8-9 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 8-9 can be implemented manually or as any combination(s) of any of the foregoing techniques, for example, any combination of firmware, software, discrete logic and/or hardware. Further, although the example processes of FIGS. 8-9 are described with reference to the flow diagrams of FIGS. 8-9, other methods of implementing the processes of FIGS. 8-9 may be employed. For example, the order of execution of the blocks can be changed, and/or some of the blocks described may be changed, eliminated, sub-divided, or combined. Additionally, any or all of the example processes of FIGS. 8-9 can be performed sequentially and/or in parallel by, for example, separate processing threads, processors, devices, discrete logic, circuits, etc.

FIG. 8 depicts a flow diagram for an example method 800 for collaborative communication including automated command recognition and execution. At block 810, a collaboration and/or other communication session is initiated between two or more participants. For example, a first user at a PACS workstation can initiate an electronic messaging session with a second user having a smart phone. The communication session can be a text-based messaging session, an audio chat session, a video conference, etc. The first and/or second user can contribute text, hyperlink and/or other reference to content, voice, gesture, image, etc., as part of the communication, for example. In certain examples, information, functionality, etc., can be prefetched for the communication session based on user identification, context, access device, etc.

For example, a radiologist is reading and annotating an image and would like to consult with a specialist before reporting on the image. The radiologist launches a consultation application to select and connect with the specialist(s) via a mobile device, workstation, etc. In certain examples, a collaboration user may have a plurality of devices associated with a user profile(s). The communication session may determine which associated device is in use by the user at the time and/or may be most likely to reach the user, and/or the user initiating communication may manual select a communication path, for example. In certain examples, the communication session may suggest and/or otherwise determine the best users to match in a collaboration based on a type of case, etc.

At block 820, a communication is provided by a user in the collaboration session. The communication can be a typed word or phrase, a spoken word or phrase, a gesture, an image, and icon, etc., entered by a user as part of communication in the collaboration session, for example.

At block 830, the communication is automatically processed to identify one or more commands in the communication. For example, a collaboration engine examines an entered phrase and recognizes the phrase as one or more commands (e.g., open a document, go to a specified image, apply a specified function/operation to a specified image, etc.).

At block 840, the one or more identified commands are executed. For example, as directed by the radiologist communicating from his or her workstation, an image open and operation command can be executed on the image that the specialist is viewing on his or her smartphone. The commands can be executed at one or more of the access devices of the collaborating users, an external clinical system, etc.

At block 850, result(s) of the executed command(s) are displayed to the collaborating uses. For example, an image manipulation instructed in the one or more commands is displayed in the collaboration session between the radiologist and the specialist.

At block 860, further action is facilitated within the collaboration session. For example, the specialist can trigger further review and manipulation of the image that has been manipulated according to the command(s) from the radiologist.

As described herein, the method 800 can be implemented using a computer workstation, laptop, handheld, smartphone, and/or other mobile device in one or more combinations of hardware, software, and/or firmware, for example. The method 800 can operate with a mobile device and/or workstation in conjunction with one or more external systems (e.g., data sources, healthcare information systems (RIS, PACS, CVIS, HIS, etc.), archives, imaging modalities, etc.), for example. One or more components of the method 800 can be reordered, eliminated, and/or repeated based on a particular implementation, for example.

FIG. 9 depicts a flow diagram for an example method 900 for processing communication input to identify one or more commands for execution. At block 910, a message is received. At block 920, using a grammar converter 925, the received message is compiled. At block 930, a syntax analysis is performed on the compiled message using a regular expression dictionary 935. For example, an incoming message is parsed and mapped to an expected regular expression. In some examples, one or many regular expressions can link to an application action.

At block 940, an application action to which an expected regular expression corresponds is generated. For example, a uniform resource locator (URL) for a corresponding action is generated. The URL can be generated based on RFC internet protocol standards to map to an application interface, for example. RFC-compliant URLs can help allow extensibility and versioning management, for example. Additionally, at block 950, a match probability is computed for the detected regular expression. For example, a parsed incoming message (e.g., SMS, email, embedded sharing session instant message, etc.) is evaluated to compute a match probability for regular expression detection.

At block 960, the URL is executed. At 970, application compatibility of the application action URL constructed from the compiled message is evaluated based on a compatible regular expression dictionary 975, for example.

Figure 10:
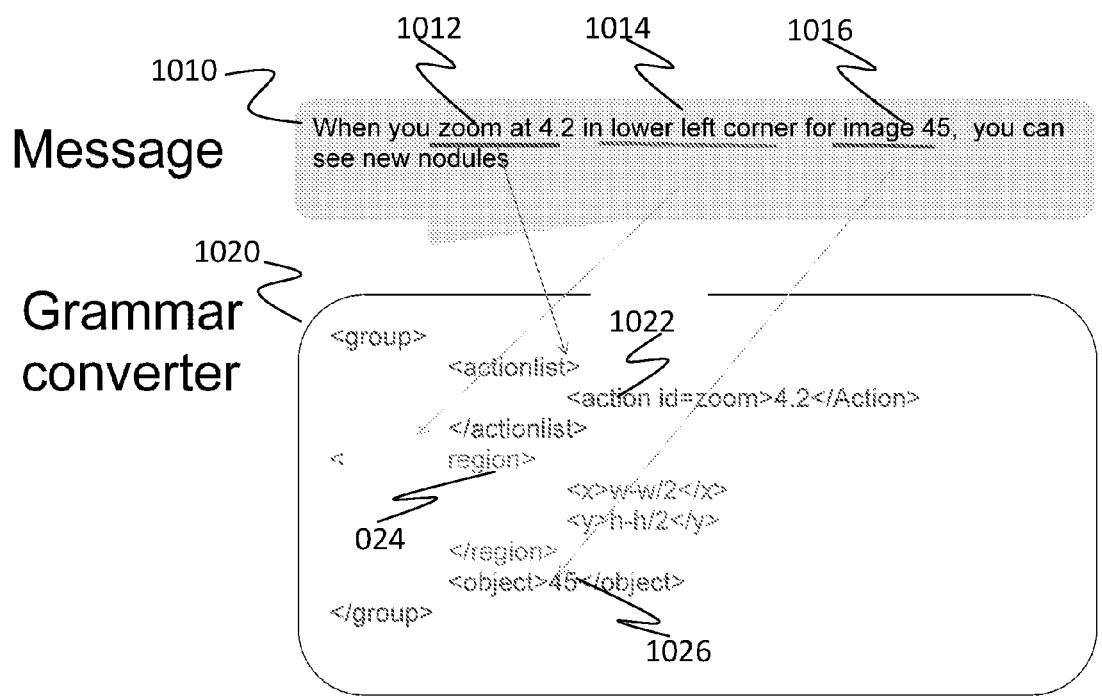
FIGS. 10-12 illustrate example message parsing and analysis for action URL generation.
Figure 11:
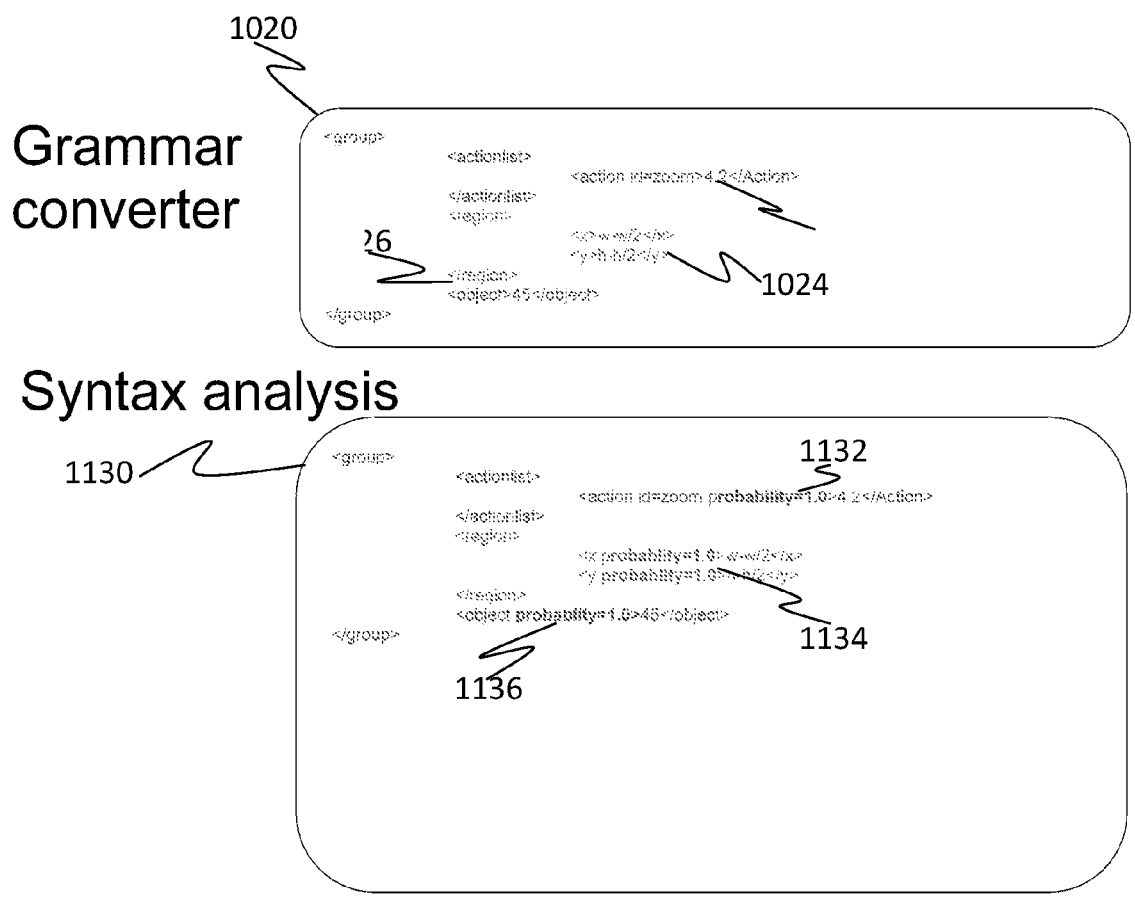
Figure 12:
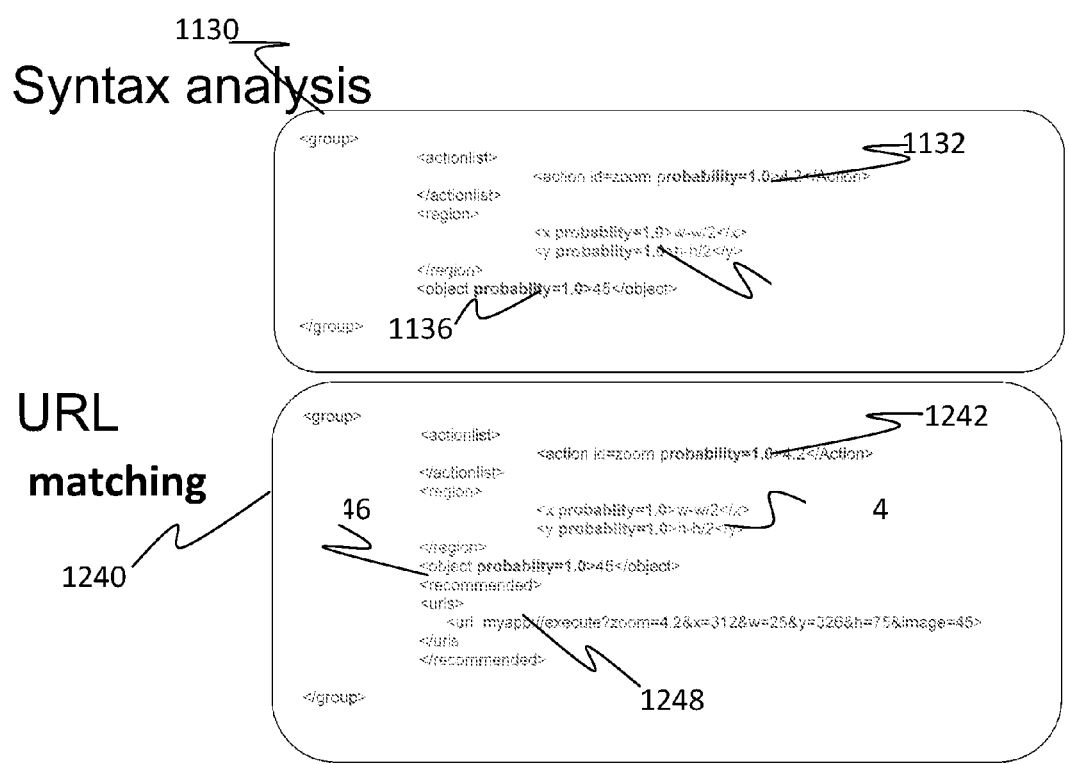

FIGS. 10-12 illustrate example message parsing and analysis for action URL generation, such as using the method 900 described above. As shown in example FIG. 10, a message 1010 is parsed to identify a plurality of instruction segments 1012, 1014, 1016. A grammar converter 1020 maps the instruction segments 1012, 1014, 1016 to elements 1022, 1024, 1026, respectively.

As shown in the example of FIG. 11, the grammar converter 1020 provides regular expression elements 1022, 1024, 1026 to a syntax analyzer 1130. The syntax analyzer 1130 computes a probability of a match 1132, 1134, 1136 for each expression 1022, 1024, 1026. A shown in the example of FIG. 12, URL matching 1240 is conducted based on the syntax analysis 1130 to generate a URL 1148 associated with one or more application actions based on expressions and probabilities 1242, 1244, 1246.

Figure 13:
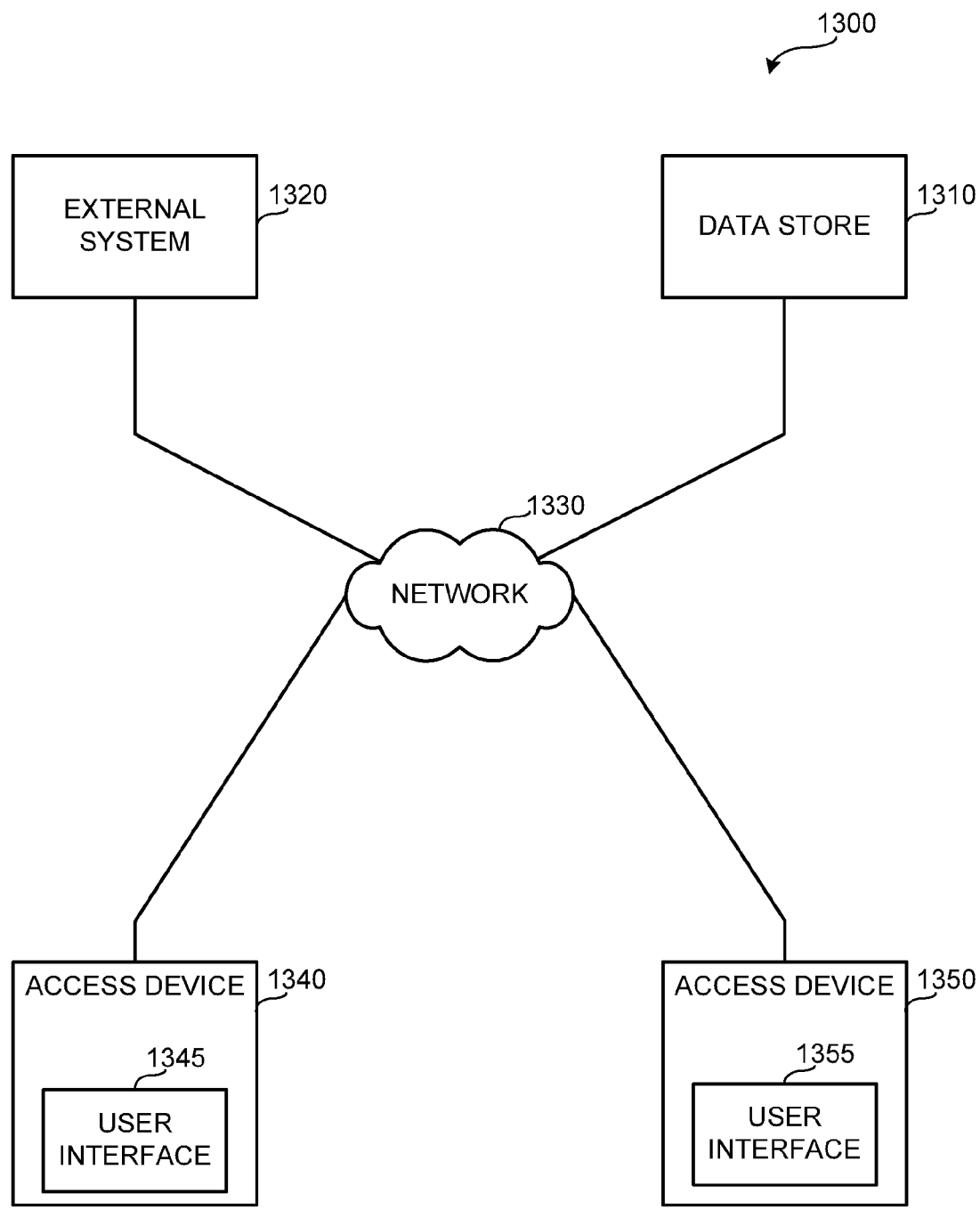
FIG. 13 depicts an example clinical enterprise system for use with systems, apparatus, and methods described herein.

Systems and methods described above can be included in a clinical enterprise system, such as example clinical enterprise system 1300 depicted in FIG. 13. The system 1300 includes a data source 1310, an external system 1320, a network 1330, a first access device 1340 with a first user interface 1345, and a second access device 1350 with a second user interface 1355. In some examples, the data source 1310 and the external system 1320 can be implemented in a single system. In some examples multiple data sources 1310 and/or external systems 1320 can be in communication via the network 1330. The data source 1310 and the external system 1320 can communicate with one or more of the access devices 1340, 1350 via the network 1330. One or more of the access devices 1340, 1350 can communicate with the data source 1310 and/or the external system 1320 via the network 1330. In some examples, the access devices 1340, 1350 can communicate with one another via the network 1330 using a communication interface (e.g., a wired or wireless communications connector/connection (e.g., a card, board, cable, wire, and/or other adapter, such as Ethernet, IEEE 1394, USB, serial port, parallel port, etc.). The network 1330 can be implemented by, for example, the Internet, an intranet, a private network, a wired or wireless Local Area Network, a wired or wireless Wide Area Network, a cellular network, and/or any other suitable network.

The data source 1310 and/or the external system 1320 can provide images, reports, guidelines, best practices and/or other data to the access devices 1340, 1350 for review, options evaluation, and/or other applications. In some examples, the data source 1310 can receive information associated with a session or conference and/or other information from the access devices 1340, 1350. In some examples, the external system 1320 can receive information associated with a session or conference and/or other information from the access devices 1340, 1350. The data source 1310 and/or the external system 1320 can be implemented using a system such as a PACS, RIS, HIS, CVIS, EMR, archive, data warehouse, imaging modality (e.g., x-ray, CT, MR, ultrasound, nuclear imaging, etc.), payer system, provider scheduling system, guideline source, hospital cost data system, and/or other healthcare system.

The access devices 1340, 1350 can be implemented using a workstation (a laptop, a desktop, a tablet computer, etc.) or a mobile device, for example. Some mobile devices include smart phones (e.g., BlackBerry™, iPhone™, etc.), Mobile Internet Devices (MID), personal digital assistants, cellular phones, handheld computers, tablet computers (iPad™), etc., for example. In some examples, security standards, virtual private network access, encryption, etc., can be used to maintain a secure connection between the access devices 1340, 1350, data source 1310, and/or external system 1320 via the network 1330.

The data source 1310 can provide images and/or other data to the access device 1340, 1350. Portions, sub-portions, and/or individual images in a data set can be provided to the access device 1340, 1350 as requested by the access device 1340, 1350, for example. In certain examples, graphical representations (e.g., thumbnails and/or icons) representative of portions, sub-portions, and/or individual images in the data set are provided to the access device 1340, 1350 from the data source 1310 for display to a user in place of the underlying image data until a user requests the underlying image data for review. In some examples, the data source 1310 can also provide and/or receive results, reports, and/or other information to/from the access device 1340, 1350.

The external system 1320 can provide/receive results, reports, and/or other information to/from the access device 1340, 1350, for example. In some examples, the external system 1320 can also provide images and/or other data to the access device 1340, 1350. Portions, sub-portions, and/or individual images in a data set can be provided to the access device 1340, 1350 as requested by the access device 1340, 1350, for example. In certain examples, graphical representations (e.g., thumbnails and/or icons) representative of portions, sub-portions, and/or individual images in the data set are provided to the access device 1340, 1350 from the external system 1320 for display to a user in place of the underlying image data until a user requests the underlying image data for review.

The data source 1310 and/or external system 13230 can be implemented using a system such as a PACS, RIS, HIS, CVIS, EMR, archive, data warehouse, imaging modality (e.g., x-ray, CT, MR, ultrasound, nuclear imaging, etc.).

In some examples, the access device 1340, 1350 can be implemented using a smart phone (e.g., BlackBerry™, iPhone™, iPad™, etc.), Mobile Internet device (MID), personal digital assistant, cellular phone, handheld computer, etc. The access device 1340, 1350 includes a processor retrieving data, executing functionality, and storing data at the access device 1340, 1350, data source 1310, and/or external system 1330. The processor drives a graphical user interface (GUI) 1345, 1355 providing information and functionality to a user and receiving user input to control the device 1340, 1350, edit information, etc. The GUI 1345, 1355 can include a touch pad/screen integrated with and/or attached to the access device 1340, 1350, for example. The device 1340, 1350 includes one or more internal memories and/or other data stores including data and tools. Data storage can include any of a variety of internal and/or external memory, disk, Bluetooth remote storage communicating with the access device 1340, 1350, etc. Using user input received via the GUI 1345, 1355 as well as information and/or functionality from the data and/or tools, the processor can navigate and access images from a large data set and generate one or more reports related to activity at the access device 1340, 1350, for example. Alternatively or in addition to gesture-based navigation/manipulation, a detector, such as an accelerometer, position encoder (e.g., absolute, incremental, optical, analog, digital, etc.), global positioning sensor, and/or other sensor, etc., can be used to detect motion of the access device 1340, 1350 (e.g., shaking, rotating or twisting, left/right turn, forward/backward motion, etc.). Detected motion can be used to affect operation and/or outcomes at the access device 1340, 1350. The access device 1340, 1350 processor can include and/or communicate with a communication interface component to query, retrieve, and/or transmit data to and/or from a remote device, for example.

The access device 1340, 1350 can be configured to follow standards and protocols that mandate a description or identifier for the communicating component (including but not limited to a network device MAC address, a phone number, a GSM phone serial number, an International Mobile Equipment Identifier, and/or other device identifying feature). These identifiers can fulfill a security requirement for device authentication. The identifier is used in combination with a front-end user interface component that leverages an input device such as but not limited to; Personal Identification Number, Keyword, Drawing/Writing a signature (including but not limited to; a textual drawing, drawing a symbol, drawing a pattern, performing a gesture, etc.), etc., to provide a quick, natural, and intuitive method of authentication. Feedback can be provided to the user regarding successful/unsuccessful authentication through display of animation effects on a mobile device user interface. For example, the device can produce a shaking of the screen when user authentication fails. Security standards, virtual private network access, encryption, etc., can be used to maintain a secure connection.

For example, an end user launches a secure application (including but not limited to a clinical application requiring a degree of security). The application reads the unique identifying features of the device and performs an authentication "hand-shake" with the server or data-providing system. This process is automated with no user input or interaction required. After the device has been authenticated, the user is presented with an application/user level authentication screen (including but not limited to a personal identification number (PIN), password/passcode, gesture, etc.) to identify to the application that the user is indeed a valid user. This feature functions as a method to provide device level security as well as an ability to lock the device (e.g., if the user wishes to temporary lock the device but not logout/shutdown the application), for example.

Figure 14:
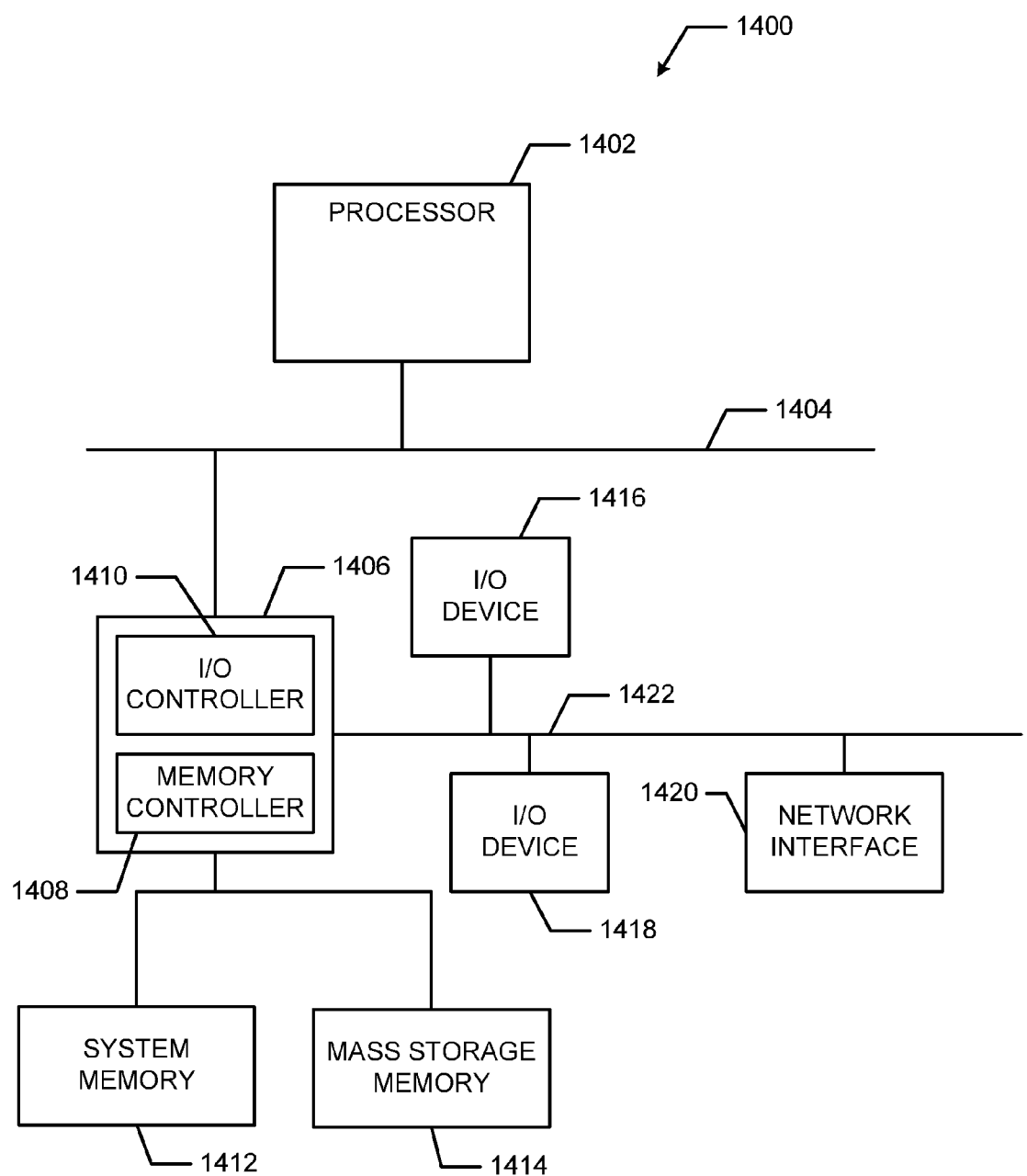
FIG. 14 is a block diagram of an example processor system that may be used to implement the systems, apparatus and methods described herein.

FIG. 14 is a block diagram of an example processor system 1410 that may be used to implement the systems, apparatus and methods described herein. As shown in FIG. 14, the processor system 1410 includes a processor 1412 that is coupled to an interconnection bus 1414. The processor 1412 may be any suitable processor, processing unit or microprocessor. Although not shown in FIG. 14, the system 1410 may be a multi-processor system and, thus, may include one or more additional processors that are identical or similar to the processor 1412 and that are communicatively coupled to the interconnection bus 1414.

The processor 1412 of FIG. 14 is coupled to a chipset 1418, which includes a memory controller 1420 and an input/output (I/O) controller 1422. As is well known, a chipset typically provides I/O and memory management functions as well as a plurality of general purpose and/or special purpose registers, timers, etc. that are accessible or used by one or more processors coupled to the chipset 1418. The memory controller 1420 performs functions that enable the processor 1412 (or processors if there are multiple processors) to access a system memory 1424 and a mass storage memory 1425.

The system memory 1424 may include any desired type of volatile and/or non-volatile memory such as, for example, static random access memory (SRAM), dynamic random access memory (DRAM), flash memory, read-only memory (ROM), etc. The mass storage memory 1425 may include any desired type of mass storage device including hard disk drives, optical drives, tape storage devices, etc.

The I/O controller 1422 performs functions that enable the processor 1412 to communicate with peripheral input/output (I/O) devices 1426 and 1428 and a network interface 1430 via an I/O bus 1432. The I/O devices 1426 and 1428 may be any desired type of I/O device such as, for example, a keyboard, a video display or monitor, a mouse, etc. The network interface 1430 may be, for example, an Ethernet device, an asynchronous transfer mode (ATM) device, an 802.11 device, a DSL modem, a cable modem, a cellular modem, etc. that enables the processor system 1410 to communicate with another processor system.

While the memory controller 1420 and the I/O controller 1422 are depicted in FIG. 14 as separate blocks within the chipset 1418, the functions performed by these blocks may be integrated within a single semiconductor circuit or may be implemented using two or more separate integrated circuits.

Thus, certain examples provide systems, apparatus, and methods for interactive communication and collaboration between two or more users via a variety of communication platforms (e.g., workstation, handheld, etc.). Certain examples automatically identify words, phrases, icons, etc., inserted by a collaborator into a communication in the session and trigger corresponding actions based on the identified content. Certain examples help to alleviate manual steps to access applications, content, functionality, etc., for the benefit of all users in a remote collaboration session.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN), a wide area network (WAN), a wireless network, a cellular phone network, etc., that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for automated command recognition and execution in collaborative communication, said method comprising:
    accepting a communication input provided by a first user in an electronic collaboration session displayed to the first user and at least one collaborator regarding clinical content;
    automatically performing a syntactic analysis of the input to parse the input to identify one or more instructions corresponding to the input;
    automatically executing the identified one or more instructions with respect to content associated with the collaboration session; and
    providing results of the execution of the identified one or more instructions to the at least one collaborator in the collaboration session.

2. The method of claim 1, wherein the content comprises a radiology image and wherein the one or more instructions instruct one or more actions to be taken with respect to the radiology image.

3. The method of claim 1, wherein the communication input comprises one or more words.

4. The method of claim 1, wherein the communication input comprises at least one of an icon and a symbol.

5. The method of claim 1, wherein the communication input comprises an audio input.

6. The method of claim 1, wherein one or more collaborators are organized and associated according to a type of communication device.

7. The method of claim 6, wherein the type of communication device comprises at least one of a mobile device and a computer workstation.

8. The method of claim 1, wherein the content resides at a clinical subsystem.

9. The method of claim 1, further comprising facilitating further interaction by a collaborator with the content following execution of the one or more instructions.

10. The method of claim 1, wherein any of a plurality of collaborators can provide the input in the collaboration session.

11. A tangible computer-readable storage medium having a set of instructions stored thereon which, when executed, instruct a processor to implement a method for automated command recognition and execution in collaborative communication, said method comprising:
    accepting a communication input provided by a first user in an electronic collaboration session displayed to the first user and at least one collaborator regarding clinical content;
    automatically performing a syntactic analysis of the input to parse the input to identify one or more instructions corresponding to the input;
    automatically executing the identified one or more instructions with respect to content associated with the collaboration session; and
    providing results of the execution of the identified one or more instructions to the at least one collaborator in the collaboration session.

12. The computer-readable storage medium of claim 11, wherein the content comprises a radiology image and wherein the one or more instructions instruct one or more actions to be taken with respect to the radiology image.

13. The computer-readable storage medium of claim 11, wherein the communication input comprises one or more words.

14. The computer-readable storage medium of claim 11, wherein the communication input comprises at least one of an icon and a symbol.

15. The computer-readable storage medium of claim 11, wherein the content resides at a clinical subsystem.

16. The computer-readable storage medium of claim 11, further comprising facilitating further interaction by a collaborator with the content following execution of the one or more instructions.

17. A collaboration system to facilitate automated command recognition and execution in collaborative communication, said system comprising:
    a communication interface to accept a communication input provided by a first user in an electronic collaboration session displayed to the first user and at least one collaborator regarding clinical content; and a collaboration engine to automatically perform a syntactic analysis of the input to parse the input to identify one or more instructions corresponding to the input and to automatically execute the identified one or more instructions with respect to content associated with the collaboration session, the collaboration engine to provide results of the execution of the identified one or more instructions to the at least one collaborator in the collaboration session.

18. The system of claim 17, wherein the content comprises a radiology image and wherein the one or more instructions instruct one or more actions to be taken with respect to the radiology image.

19. The system of claim 17, wherein one or more collaborators are organized and associated according to a type of communication device.

20. The system of claim 19, wherein the type of communication device comprises at least one of a mobile device and a computer workstation.

21. The system of claim 17, wherein the content resides at a clinical subsystem.

22. The system of claim 17, wherein the collaboration engine is to further facilitate additional interaction by a collaborator with the content following execution of the one or more instructions.

23. The system of claim 17, wherein any of a plurality of collaborators can provide the input in the collaboration session.

\* \* \* \* \*